United States Patent [19]

Burchfield

[11] 4,426,528

[45] Jan. 17, 1984

[54] PURIFICATION OF SYN-(2-AMINOTHIAZOL-4-YL)METHOX-YIMINO)ACETIC ACID

[75] Inventor: Robert W. Burchfield, Greenwood, Ind.

[73] Assignee: Eli Lilly and Company, Indianapolis, Ind.

[21] Appl. No.: 364,356

[22] Filed: Apr. 1, 1982

[51] Int. Cl.³ .......................................... C07D 277/38
[52] U.S. Cl. .................................................. 548/194
[58] Field of Search ........................................ 548/194

[56] References Cited

U.S. PATENT DOCUMENTS

| | | | |
|---|---|---|---|
| 3,925,372 | 12/1975 | Chauvette | 260/243 |
| 4,098,888 | 7/1978 | Ochiai | 424/246 |
| 4,152,432 | 5/1979 | Heymes et al. | 424/246 |
| 4,152,433 | 5/1979 | Kamiya | 424/246 |
| 4,252,951 | 2/1981 | Jackson et al. | 544/54 |

*Primary Examiner*—Robert Gerstl
*Attorney, Agent, or Firm*—Joseph A. Jones; Arthur R. Whale

[57] ABSTRACT

Syn-(2-aminothiazol-4-yl)(methoxyimino)acetic acid is purified by formation of its crystalline bis-dimethylacetamide solvate.

2 Claims, No Drawings

PURIFICATION OF SYN-(2-AMINOTHIAZOL-4-YL)METHOXYIMINO)ACETIC ACID

BACKGROUND OF THE INVENTION

1. Field of the Invention

This invention concerns synthetic pharmaceutical chemistry, and provides a new solvate used in a process for purifying syn-(2-aminothiazol-4-yl)(methoxyimino) acetic acid. A bis-dimethylacetamide solvate of the acetic acid is formed and precipitated in excellent purity and yield.

2. State of the Art

The thiazolyl acetic acid which is purified by the present process is a known compound used as an intermediate in preparing a large class of cephalosporin pharmaceuticals, the acyl side chain of which is formed from the thiazolyl acetic acid. Numerous patents and publications have appeared. For example, U.S. Pat. No. 4,152,433 of Fujisawa Co. and U.S. Pat. No. 4,098,888 of Takeda Chemical Industries show the synthesis of various cephalosporin compounds making use of the thiazolylacetic acid as an intermediate. Often the amino group of the substituted acetic acid is blocked by a group such as trityl or the like, and the acid is usually converted into an active form such as the acid chloride or the like for use as an acylating agent.

The formation of solvates is known to be a highly individualistic effect. The ability of a given compound to form a solvate is not predictable, so far as applicant knows, and to his knowledge and belief nothing in the literature indicates that the thiazolyl acetic acid which is the subject of this invention can form a solvate with dimethylacetamide, or with any solvent.

SUMMARY OF THE INVENTION

This invention provides the bis-dimethylacetamide solvate of syn-(2-aminothiazol-4-yl) (methoxyimino) acetic acid, which is used in the method of purifying the thiazolyl acetic acid also provided by the invention. That method comprises dissolving the impure solid acid in dimethylacetamide, and crystallizing the bis-dimethylacetamide solvate from the solution.

DESCRIPTION OF THE PREFERRED EMBODIMENTS

In this document, all temperatures are expressed in degrees Celsius.

The thiazolyl acetic acid which is purified by the process of this invention is of the formula

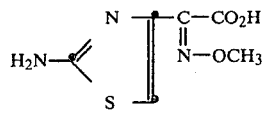

It is important that the methoxyimino group be in the configuration shown, known as the syn configuration, because it is now well known that the cephalosporins formed from the acid are much more biologically active when the imino group is in the syn configuration.

The bis-dimethylacetamide (DMAC) solvate of the acid is readily formed by merely dissolving the impure solid acid in DMAC, and crystallizing the solvate from the solution. The crystallization may be done by the usual methods, such as cooling or chilling a solution made at an elevated temperature, or evaporating part of the DMAC from the solution.

The method of purification is especially useful for purifying water-wet acid. It is found that water is particularly difficult to remove from the acid, and normal drying techniques are inadequate. The purification method of this invention, however, precipitates the disolvate quite free of water, even when the impure acid contains several percent of water, and accordingly produces the acid in a form which is much more appropriate for further processing.

The present method also is particularly efficient in purifying the acid from the dark, tarry contaminants which usually are formed in its synthesis. The solvate precipitates as cubic white crystals, leaving the dark matter in the DMAC phase. It will be understood that dark-colored impurities are very undesirable in intermediates to be used for synthesis, especially in pharmaceutical intermediates.

The formation of the DMAC solvate is a simple crystallization from DMAC. It has been found to be most efficient to use an amount of DMAC which is approximately twice the amount of the impure thiazolyl acetic acid, and to dissolve the acid at about 40°-60° with stirring. The concentration and temperature are not critical, however, and may be varied over a wide range. The solution is then stirred and cooled to about 0°-10°, and the disolvate precipitates in very pure form. It is desirable to seed the solution with disolvate, if it is available from previous lots, to assist the crystallization.

The formation and precipitation of the disolvate are analogous to other crystallization procedures. Thus, the yield of disolvate is increased by higher concentration of the acid and by lower crystallization temperature, and decreased by lower concentration and higher crystallization temperature. The composition and purity of the precipitated disolvate are not affected by the conditions, however. Accordingly, the chemist can vary the amount of DMAC and the temperatures freely.

For example, concentrations of the acid in the range of from about 5% to about 50% by weight may be used as may be desired in a given case. The DMAC solution of the acid may be heated, to obtain dissolution, to temperatures in the range of from about the ambient temperature to about 100°, or even higher, using elevated pressures as necessary to suppress boiling. The solution may be cooled, to obtain crystallization, to any temperature short of that which completely solidifies the solution, such as from about −50° to about the ambient temperature.

The precipitated disolvate is easily removed from the liquid phase by filtration or centrifugation, and can be washed on the filter with DMAC or other solvents to remove liquid phase containing the impurities which have been removed from the acid.

The solvate of this invention is a true solvate having a fixed composition, but it is not tightly bound. The DMAC is easily removed from the solvate with heat and vacuum, if the dry pure acid is needed for use as an intermediate. Of course, if the solvent for the next synthetic step is DMAC, or if a small amount of DMAC is acceptable in the reaction mixture, the solvate may be used as the intermediate without further treatment.

The DMAC is readily removed from the solvate of this invention by simple contact with water, or with virtually any convenient organic solvent. It is unnecessary to dissolve the solvate to remove the DMAC. As the examples below illustrate, mere slurrying of the solvate in an organic solvent or water will remove the DMAC into the solvent phase, so that the acid may be obtained in pure form by filtering.

Any of many organic solvents can be used to release DMAC from the solvate. For example, ethers such as diethyl ether, tetrahydrofuran and diisopropyl ether, alcohols such as methanol, ethanol and butanol, alkanes such as hexane, octane and the like, haloalkanes such as dichloromethane, 1,2-dichloroethane and trichloroethane, aromatics and halo-aromatics such as benzene, toluene, xylene, chlorobenzene, bromobenzene and the dichlorobenzenes, amides such as dimethylformamide, and ketones such as acetone, methyl ethyl ketone and methyl isobutyl ketone may be used. Esters, especially ethyl acetate, are preferred; propyl acetate, methyl propionate, benzyl acetate and the like are also useful.

Thus, the solvate may be used as an intermediate, just as it is precipitated, if a small amount of DMAC is acceptable in the reaction mixture in which it is to serve as an intermediate. If DMAC is not acceptable, the DMAC can be removed by drying, or displaced with water, if the next reaction mixture is aqueous, or with any convenient organic solvent, if water is not acceptable in that next reaction mixture.

The following examples further illustrate the invention.

EXAMPLE 1

A 56.8 g. portion of impure syn-(2-aminothiazol-4-yl)(methoxyimino)acetic acid containing 12% water and other impurities was dissolved in 113.6 ml. of DMAC under nitrogen. The mixture was heated to 55° to dissolve the acid, and it was then allowed to cool to ambient temperature with stirring. A small amount of the disolvate was added as seeds while the temperature was falling. The mixture was then cooled to 10° and filtered, and the disolvate was washed with 400 ml. of diethyl ether. The solids were identified as the DMAC disolvate by nuclear magnetic resonance analysis. By comparison of the methyl integral assigned to DMAC ($\delta 2.0$) with the integral of the methoxyimino signal ($\delta 3.9$) of syn-(2-aminothiazol-4-yl)(methoxyimino) acetic acid a constant ratio (2:1, DMAC: aminothiazole acid) was obtained from the NMR spectrum. This ratio indicates that the sample contains 46% DMAC, confirming the disolvate composition.

The disolvate was suspended in 400 ml. of ethyl acetate and stirred for 2 hours at 45° under nitrogen. The suspension was then cooled to 10° and filtered, and the solids were washed with 800 ml. of additional ethyl acetate. The washed solids were dried for two and a half hours in air at 50°, and 44.4 g. of dried product was obtained, which was identified as 97.26% pure product containing 1.35% of DMAC and 1.37% of ethyl acetate. The water content of the product was 0.36% by Karl Fischer analysis.

EXAMPLE 2

A 113.4 g. portion of syn-(2-aminothiazol-4-yl) (methoxyimino)acetic acid containing 11.8% water and other impurities was dissolved in 227 ml. of DMAC at 50° under nitrogen. It was cooled, with stirring, and crystallization began at 45°. The mixture was stirred at that temperature for 1 hour with occasional seeding with disolvate, and then the mixture was allowed to cool to ambient temperature. It was then chilled to 5° and stirred for 30 minutes at that temperature, and filtered. The solid disolvate was washed with 200 ml. of 1:4 DMAC:ethyl acetate, 200 ml. of 1:19 DMAC:ethyl acetate and finally with 400 ml. of ethyl acetate. The solid disolvate was perfectly white and the cake was crystalline and easily handled. The solids were added to 1 liter of ethyl acetate and stirred overnight at ambient temperature to break the disolvate. The mixture was filtered, and the solids were washed with 500 ml. of ethyl acetate and air dried for 3 hours at 50° to obtain 72.7 g. of product containing 0.72% water by Karl Fischer analysis.

I claim:

1. The bis-dimethylacetamide solvate of syn-(2-aminothiazol-4-yl)(methoxyimino)acetic acid.

2. A process for purifying syn-(2-aminothiazol-4-yl) (methoxyimino) acetic acid comprising dissolving the solid impure acid in dimethylacetamide, and crystallizing and separating the bis-dimethylacetamide solvate from the solution.

* * * * *